United States Patent [19]
Martens

[11] Patent Number: 6,055,862
[45] Date of Patent: May 2, 2000

[54] METHOD OF AND AN APPARATUS FOR DETECTING, IDENTIFYING AND RECORDING THE LOCATION OF DEFECTS IN A RAILWAY RAIL

[75] Inventor: George D. Martens, New Milford, Conn.

[73] Assignee: Herzog Services, Inc., St. Joseph, Mo.

[21] Appl. No.: 08/975,299

[22] Filed: Nov. 20, 1997

Related U.S. Application Data

[63] Continuation of application No. 08/661,061, Jun. 10, 1996, abandoned.

[51] Int. Cl.[7] .................................................... G01N 29/00
[52] U.S. Cl. ............................... 73/632; 73/633; 73/635; 73/636
[58] Field of Search .............................. 73/632, 633, 635, 73/636, 639, 602, 644

[56] References Cited

U.S. PATENT DOCUMENTS

| | | | |
|---|---|---|---|
| 3,771,354 | 11/1973 | Miller | 73/639 |
| 4,165,648 | 8/1979 | Pagano | 73/625 |
| 4,174,636 | 11/1979 | Pagano | 73/636 |
| 4,235,112 | 11/1980 | Kaiser | 73/634 |
| 4,429,576 | 2/1984 | Norris | 73/636 |
| 4,457,178 | 7/1984 | Turbe et al. | 73/636 |
| 4,468,966 | 9/1984 | Bradshaw | 73/636 |
| 4,487,071 | 12/1984 | Pagano et al. | 73/612 |
| 4,593,569 | 6/1986 | Joy | 73/636 |
| 4,662,224 | 5/1987 | Turbe | 73/636 |
| 4,700,574 | 10/1987 | Turbe | 73/636 |
| 5,020,371 | 6/1991 | Panetti | 73/636 |
| 5,419,196 | 5/1995 | Havira et al. | 73/636 |

*Primary Examiner*—Hezron Williams
*Assistant Examiner*—Richard A. Moller
*Attorney, Agent, or Firm*—James Ray & Associates

[57] ABSTRACT

Method and apparatus for ultrasonic inspection of an object. A tire is mounted for rolling along the surface of the object. It contains a liquid and a transducer assembly. The transducer assembly is positioned in the tire adjacent a portion of the surface of the tire in contact with the object. The liquid and the surface of the tire in contact with the object provide an acoustic bridge between the transducer assembly and the object. An electric signal processing system is connected to the transducer assembly. It generates electric signals which are converted to acoustic signals in the transducer assembly to place acoustic signals in the object. Acoustic signals returned from the object are converted to electric signals by the transducer assembly, and are processed in the electric signal processing system to indicate flaws in the object.

32 Claims, 4 Drawing Sheets

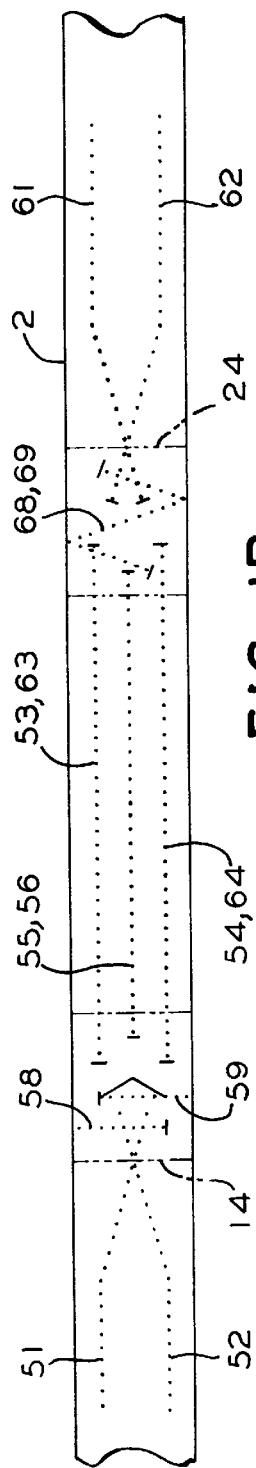
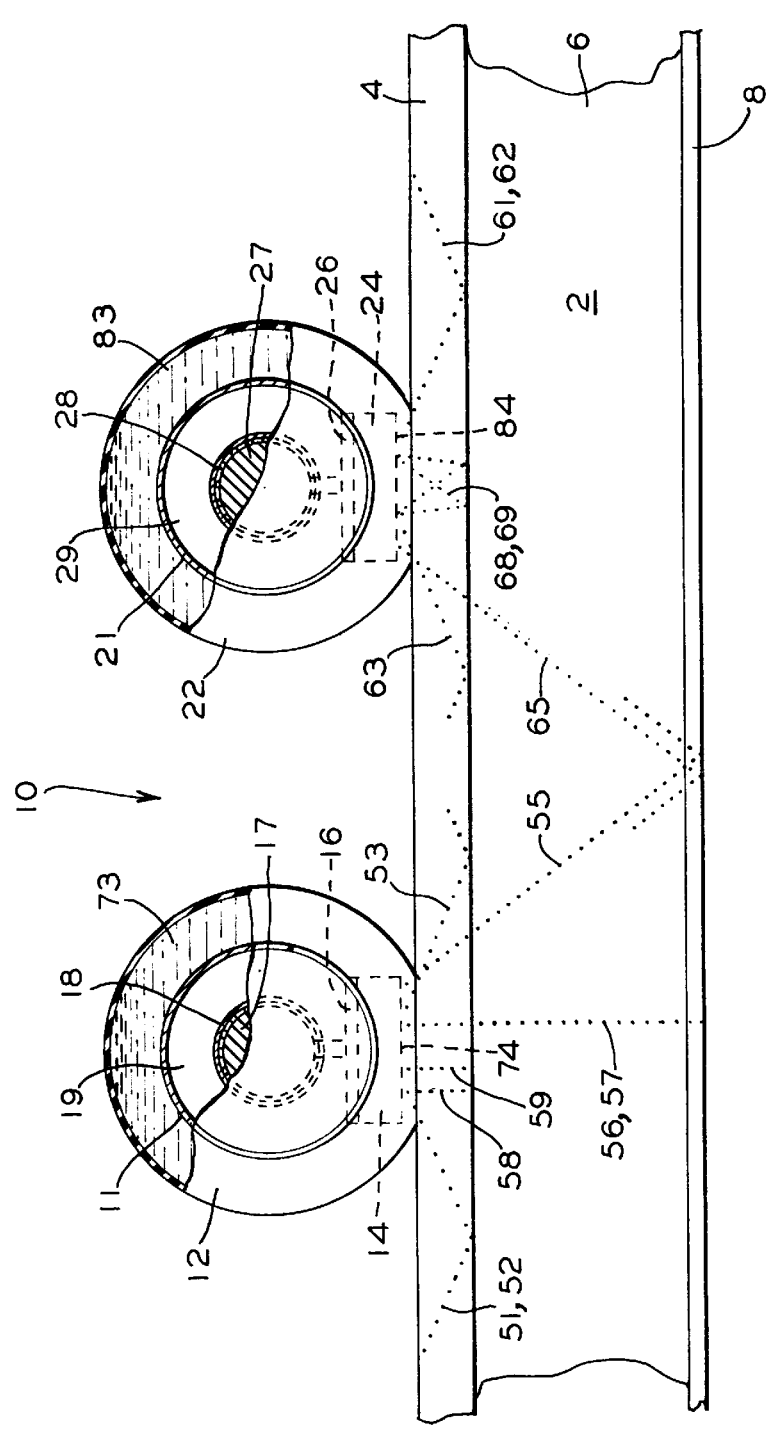
FIG. 1B
FIG. 1A

METHOD OF AND AN APPARATUS FOR DETECTING, IDENTIFYING AND RECORDING THE LOCATION OF DEFECTS IN A RAILWAY RAIL

CROSS-REFERENCE TO RELATED APPLICATIONS

This application is a continuation of patent application Ser. No. 08/661,061, filed Jun. 10, 1996, now abandoned.

FIELD OF THE INVENTION

The present invention relates, in general, to nondestructive type testing for certain predetermined types of undesirable flaws and/or other detrimental type defects which may be present in at least one of the rail portions of a railroad track structure and, more particularly, this invention relates to a mobile type apparatus that will ultrasonically detect these detrimental flaws and/or other type defects in such rail portion and then identify with a mark the location of such defects when they are detected by such apparatus and, additionally, record the particular location of such defects that have been detected for possible future reference and, still more specifically, the instant invention relates to a relatively fast and reliable method of detecting, identifying and recording the location of such undesirable defects that are detected by the apparatus as it travels over the rail.

BACKGROUND OF THE INVENTION

Prior to the conception and development of the present invention, as is generally well recognized in the railroad industry, the rails that are to be used in construction of a new track structure and/or the repairing of an existing track structure will normally have undergone some testing for certain known types of undesirable defects, such as slag inclusions, by the manufacturer of such rail prior to the rails being shipped to the railroad and/or to the track builder. Such testing may include, for example, in line X-rays being taken as the rail is being rolled.

Nevertheless, during their normal use and as would be expected, the rail portions of most track structures will be subjected to rather sever, as well as, uncontrollable environmental conditions. These rather sever environmental conditions, over a relatively long period of time, may ultimately result in such rail developing certain detrimental flaws. Such flaws may include, for example only, cracks.

In addition, in today's modern railroad industry, the rail portion of such track structures will quite often be required to support rather heavy loads being carried by modern freight cars. Furthermore, these heavy loads are travelling at relatively high speeds. It would not be uncommon for these freight cars, when they are fully loaded with cargo, to weigh up to generally about 125 tons. Such relatively heavy loads and high speeds can, also, result in undesirable damage to such rail portions of the track structure. Such damage, for example, may include stress fractures.

It would be expected, therefore, that if these detrimental defects were not timely detected and, likewise, if they are left unrepaired such defects could lead to some rather catastrophic disasters, such as, a train derailment.

As is equally well known, such train derailments are not only costly to the railroad industry from the standpoint of the damage that will likely be incurred to both the cargo being transported and to the railway equipment itself, but, even more importantly, such train derailments may also involve some rather serious injuries, or even worse death, to railway personnel and/or other persons who may be in the vicinity of a train derailment.

It is further well known that a relatively large number of these train derailments have resulted in the undesirable and often costly evacuation of nearby homes and businesses. Such evacuation may be required, for example, when the cargo being transported involves certain highly hazardous chemical products. These hazardous chemical products will generally include both certain types of liquids, such as corrosive acids, and certain types of toxic gases, such as chlorine.

To detect such flaws and defects, ultrasonic testing has been employed. Vehicles have been built which travel along the track and continuously perform ultrasonic testing of the track. These vehicles carry test units which apply ultrasonic signals to the rails, receive ultrasonic signals back from the rails, and provide indications of flaws and defects.

Some of these test units employ sleds which slide along the rails. Acoustic transducers are located in the sleds. These transducers apply ultrasonic signals to the rails, and receive ultrasonic signals back from the rails. Water is applied to the rails ahead of the sleds to serve as an acoustic bridge between the sleds and the rails. This approach has the disadvantage that it has not been possible to obtain good, constant acoustic contact between the sleds and the rails in heavily curve worn rail. Also such sleds require large amounts of water for adequate sled to rail coupling.

Another approach is to employ small, thin-walled tires which roll along the rails. They are pressed down against the rail so as to have a flat area in contact with the rail. These tires contain acoustic transducers and are filled with a liquid, usually a water-antifreeze solution. The transducers are arranged in an arc to produce acoustic beams which travel through the liquid and are directed toward the center of the flat area. The high frequency electrical transducers are pulsed with energy and the beams intersect in the flat area. The beams then pass through the material of the tire into the rail, are reflected from defects in the rail, the reflected beams returning to the transducers and being detected.

This approach has one disadvantage that only a few transducers can be located in the arc due to spacial considerations. Also, the angles of the acoustic beams produced by the transducers are dictated by their positions in the arc. Another disadvantage is that when the beams strike the inside surface of the tire at the center of the flat area, they generate reflections which cause echoes which reverberate for some time. This limits the times during which signals obtained back from the transducers can be used as indications of beams reflected back from defects and imperfections in the rail.

An additional disadvantage is that for some observations, precise control of the angle of the acoustic beams in the rail is required. This is particularly true for beams which travel along the rail at shallow angles. In this approach, since the beams are generated in liquid, and then, after passing through the tire material, continue in the steel, the beams are refracted by the differing indices of refraction of the acoustic beam between the liquid and steel. Hence, the angle of refraction is affected by the speed of sound in the liquid. For most compositions, this speed depends on the temperature, so the angle of the refracted beam depends on the temperature. To prevent this, it is necessary to use a weak anti-freeze solution for which the speed of sound is temperature invariant. With this weak solution, it is not possible to operate in cold weather.

SUMMARY OF THE INVENTION

The present invention, in a first aspect thereof, provides an apparatus for detecting, providing an identification mark and recording the location of certain types of defects detected in an object. Such apparatus includes engagement means such as a tire for rolling contact with the object, the tire containing a liquid. Means are connected to the tire for supporting it and for rolling it along the object. An acoustic transducer assembly is located inside the tire. Means are connected to the transducer assembly to position it in the tire which is in contact with the object. The liquid provides a coupling between the transducer assembly and the tire. In addition, the liquid acts as an acoustic bridge between the acoustic transducer assembly and the tire. An electric signal processing means is connected to the transducer assembly, the transducer assembly providing conversion of energy between electric signals in the electric signal processing means and acoustic signals in the object. The electric signals are for placing acoustic signals in the object and/or for interpretation of acoustic signals returned from the object.

According to a second aspect, the present invention provides a quick and highly reliable apparatus for ultrasonic inspection of railroad rails. The apparatus includes a vehicle for travelling along a pair of railroad rails. Engagement means such as one or more tires is attached to the vehicle, each tire making rolling contact with one of the rails. The tire contains a liquid and an acoustic transducer assembly. Means are provided for positioning the transducer assembly within the tire. An electric signal processing means is disposed on the vehicle. The electric signal processing means is connected to the transducer assembly which provides conversion of energy between electric signals in the electric signal processing means and acoustic signals in the railroad rail. The electric signals are for either placing acoustic signals in the rail, and/or for interpretation of acoustic signals returned from the rail.

In a third aspect, the present invention provides a method for ultrasonic inspection of an object. The method includes rolling an engagement means such as a tire along the surface of the object, the tire containing a liquid and a transducer assembly. The transducer assembly includes at least one transducer which is firmly attached to the transducer assembly. The method further includes applying high frequency electrical pulses to the transducer to make it generate at least one ultrasonic pulse, which creates an ultrasonic beam which passes through the transducer assembly, the liquid and the tire into the object, the beam encountering imperfections in the object and generating a back reflected acoustic signal which indicates such imperfections, a portion of the back reflected acoustic signal returning to the transducer to generate electric signals indicating the imperfections. The method further includes conveying the electric signals to an electric signal processing means to analyze the signals to define and provide an indication of the imperfections.

OBJECTS OF THE INVENTION

It is, therefore, one of the primary objects of the present invention to provide a mobile apparatus capable of detecting, identifying and recording the location of certain types of defects in the rail portion of a track structure and which will exhibit both accurate and repeatable flaw detection at travel speeds of up to and beyond 25 MPH.

Another object of the present invention is to provide a mobile apparatus capable of detecting, identifying and recording the location of certain types of defects in the rail portion of a track structure which combines a rugged mechanical design with electronic instrumentation to ensure precise defect testing results.

Still another object of the present invention is to provide a mobile apparatus capable of detecting, identifying and recording the location of certain types of defects in the rail portion of a track structure which includes a base vehicle that is readily gauge-variable to allow testing of all common track gauges that may be encountered.

Yet another object of the present invention is to provide a mobile apparatus capable of detecting, identifying and recording the location of certain types of defects in the rail portion of a track structure which is configured in such a manner to provide flexibility in testing at either high speed non-stop or normal speed immediate verification depending upon the customer's specific requirements.

A further object of the present invention is to provide a mobile apparatus capable of detecting, identifying and recording the location of certain types of defects in the rail portion of a track structure which includes on-off track hy-rail capability to give minimal traffic disruption while the test procedure is being performed, as well as rail bound usage.

It is an additional object of the present invention to provide a method of testing the rail portion of a track structure in order to detect, identify and record the location of certain types of defects which is highly reliable and can be performed at speeds of up to and beyond 25 MPH.

Still yet another object of the present invention is to provide a method of testing the rail portion of a track structure in order to detect, identify and record the location of certain types of defects which provides for a larger number of transducers than prior art systems, and hence provides more options and greater flexibility.

Yet still another object of the present invention is to provide a method of testing the rail portion of a track structure in order to detect, identify and record the location of certain types of defects which can be performed on all common gauges of track encountered.

A still further another object of the present invention is to provide a method of testing the rail portion of a track structure in order to detect, identify and record the location of certain types of defects which provides for selective monitoring of individual sensors.

An additional object of the present invention is to provide a method of testing the rail portion of a track structure in order to detect, identify and record the location of certain types of defects which can be carried out in such a manner to provide flexibility in testing at either high speed non-stop or normal speed immediate verification depending upon the customer's specific requirements.

An additional object of the present invention is to provide an apparatus for and a method of testing an object in order to detect, identify and record the location of certain types of defects which overcomes certain known disadvantages of the prior art type ultrasonic testing systems and methods.

Another object of the present invention is to provide an apparatus for testing an object in order to detect, identify and record the location of certain types of defects which provides superior acoustic contact between the transducers and the object being tested.

Yet another object of the present invention is to provide an apparatus for testing an object in order to detect, identify and record the location of certain types of defects which provides an improved mounting arrangement for the transducers in the apparatus.

Still another object of the present invention is to provide an apparatus for testing an object in order to detect, identify and record the location of certain types of defects which possesses the desirable capability of utilizing a greater number of transducers than was possible with prior art type ultrasonic testing equipment.

A further object of the present invention is to provide an apparatus for testing an object in order to detect, identify and record the location of certain types of defects which substantially eliminates interference from reflected acoustic signals within the apparatus.

It is an additional object of the present invention to provide an apparatus for testing an object in order to detect, identify and record the location of certain types of defects in which two or more transducers can be used to produce acoustic beams at substantially the same angle.

Still yet another object of the present invention is to provide an apparatus for and a method of testing an object in order to detect, identify and record the location of certain types of defects which substantially eliminates the dependence of the beam angle on the liquid composition being used as a coupling media so that a solution rich in antifreeze may be used for operation in cold weather.

A further object of the present invention is to provide an apparatus for testing an object in order to detect, identify and record the location of certain types of defects in which more transducers with more angle options may be used than is possible with the prior art configurations.

Another object of the present invention is to provide an apparatus for testing an object in order to detect, identify and record the location of certain types of defects which possesses the capability to reorient the transducers away from each other thereby avoiding unwanted noise and interaction.

Still another object of the present invention is to provide an apparatus for testing an object in order to detect, identify and record the location of certain types of defects which substantially minimizes the limitation on test time when the transducers are receiving signals back from the object in comparison to the limitation in time imposed by multiple reflections in the tire with the prior art configurations.

Yet another object of the present invention is to provide an apparatus for testing an object in order to detect, identify and record the location of certain types of defects which obtains a higher test speed by minimizing the delay time, most of which is caused in the prior art configurations by the distance the beams travel through the liquid in the tire.

An additional object of the present invention is to provide an apparatus for testing an object in order to detect, identify and record the location of certain types of defects which provides a system in which the angle at which an ultrasonic beam enters the object is only weakly affected by the speed of sound in the liquid, so that an uncompensated liquid can be used; the uncompensated liquid having sufficient antifreeze that it can operate at lower temperatures than the compensated liquid required in the prior art.

A further object of the present invention is to provide an apparatus for testing an object in order to detect, identify and record the location of certain types of defects which is capable of looking for defects which are hidden under shell in a railroad rail.

Still another object of the present invention is to provide an apparatus for testing an object in order to detect, identify and record the location of certain types of defects which can apply substantially vertical ultrasonic beams to both sides of a rail head to determine certain rail conditions, locate field welds, and aid in rail tracking.

In addition to the several objects and advantages of the present invention which have been described in some detail above, various other objects and advantages of the apparatus for and method of detecting, identifying and recording the location of defects in the rail portion of a track structure will become more readily apparent to those persons who are skilled in the rail testing art from the following more detailed description of the invention, particularly, when such description is taken in conjunction with the attached drawing Figures and with the appended claims.

BRIEF DESCRIPTION OF THE DRAWINGS

FIG. 1A is a schematic elevation view illustrating the essential features of one presently preferred two-tired embodiment of the ultrasonic testing assembly, according to the invention, as used to observe defects in a railroad rail;

FIG. 1B is a top view of the rail showing the paths followed by various acoustic beams in the rail;

Figure 2:
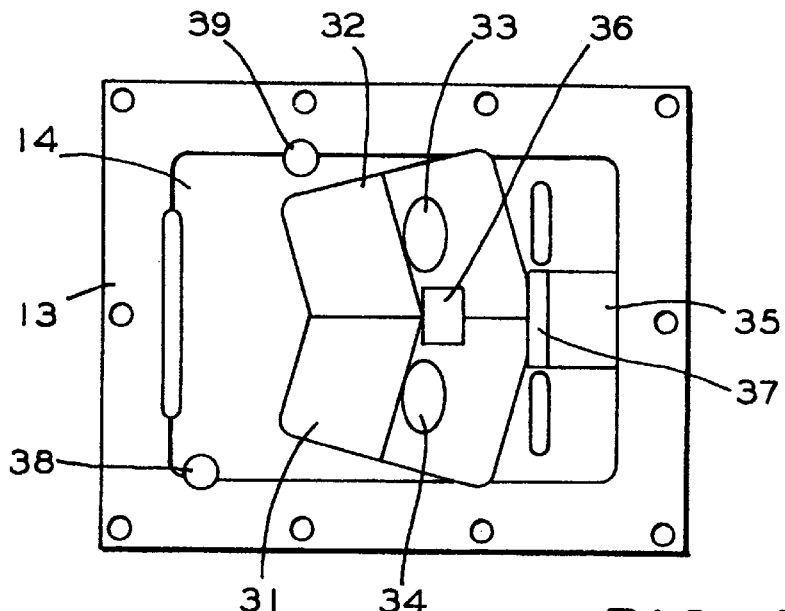
FIG. 2 is a schematic top view illustrating an acoustic transducer assembly module used in a first one of the two tires.

BRIEF DESCRIPTION OF A PRESENTLY PREFERRED AND VARIOUS ALTERNATIVE EMBODIMENTS OF THE INVENTION

Prior to proceeding to the more detailed description of the present invention, it should be noted that for the sake of clarity and understanding of the invention, identical components having identical functions have been identified with identical reference numerals throughout the several views that have been illustrated in the attached drawings.

Figure 1C:
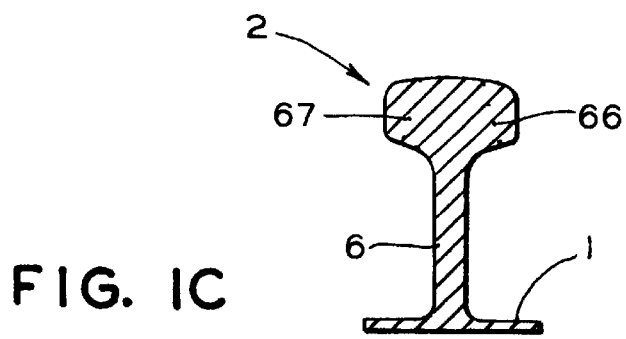
FIG. 1C is a cross section of the rail showing two of the acoustic beams.

Referring now to FIGS. 1A, 1B, and 1C, there is shown a presently most preferred embodiment of the invention. The invention, which in this embodiment has engagement means consisting of two tires, 12 and 22 is generally indicated as 10. Tire 12 contains liquid 73 and tire 22 contains liquid 83.

Tire 12 is clamped to wheel 19 at its bead 11. Wheel 19 rotates with tire 12 about axle 17 at bearing 18. Axle 17 serves as a support means to place wheel 19 in an operating position with respect to the object being examined. A seal (not shown) concentric with bearing 18 is provided to permit relative rotation of wheel 19 and axle 17 without loss of coupling liquid from the interior space of tire 12.

Tire 22 is clamped to the wheel 29 at its bead 21. Wheel 29 rotates with tire 22 about axle 27 at bearing 28. Axle 27 serves as a support means to place wheel 29 in an operating position with respect to the object being examined. A seal (not shown) concentric with bearing 28 is provided to permit relative rotation of wheel 29 and axle 27 without loss of coupling liquid from the interior space of tire 22.

Transducer assembly 14 is positioned within tire 12 by positioning means 16, which is attached to axle 17. Transducer assembly 24 is positioned within tire 22 by positioning means 26, which is attached to axle 27.

Acoustic beams produced by transducers positioned in transducer assemblies 14 and 24 are shown in FIGS. 1A, 1B, and 1C.

Acoustic beams 51 and 52 are directed approximately parallel to rail 2 from transducer assembly 14. Viewed from above, as in FIG. 1B, they cross the rail 2 at an angle of about 15 degrees. Viewed in transverse section FIG. 1A, they descend into the rail 2 at an angle of about 70 degrees from the vertical. These beams 51 and 52 provide a view of under shell defects, since they approach the under shell defects from underneath.

Acoustic beams 61 and 62 are, also, directed approximately parallel to rail 2 from transducer assembly 24. Viewed from above, as in FIG. 1B, they cross the rail at an angle of about 15 degrees. Viewed in transverse section FIG. 1A, they descend into the rail 2 at an angle of about 70 degrees from the vertical. These beams 61 and 62 provide a view of under shell defects, since they approach the under shell defects from underneath.

Acoustic beams 53 and 54 when viewed from above are seen to be parallel to the rail 2, but in elevation view FIG. 1A, they are seen to descend into the rail 2 at an angle of about 70 degrees from the vertical. The beams 53 and 54 look substantially down the rail 2 and may be used in conjunction with views from beams 51 and 52.

Acoustic beams 63 and 64 when viewed from above are seen to be parallel to the rail 2, but in elevation view FIG. 1A, they are seen to descend into the rail 2 at an angle of about 70 degrees from the vertical. The beams 63 and 64 look substantially down the rail 2 and may, for example, be used in conjunction with views from beams 61 and 62.

Beams 55 and 65 are generated by transducer assemblies 14 and 24, respectively. These beams 55 and 65 penetrate through the web 6 of rail 2 to the bottom 8 of rail 2. They show defects in the web 6 including bolt hole cracks. Beams 55 and 65, also, show weld defects and centrally located transverse defects. These beams 55 and 65 are transmitted between the two transducer assemblies 14 and 24.

Beams 56 and 57 descend in a substantially vertical direction from the transducer assembly 14 through web 6 to the bottom 8 of rail 2. Such beams 56 and 57 act as one channel. Beams 56 and 57, like beams 55 and 65 show web 6 defects, including bolt hole cracks, as well as rail head 4 and web 6 horizontals and angled defects.

Beams 66 and 67 are produced by the transducer assembly 24. They descend through the sides of the rail head 4 to the bottom of the rail head 4. The beams 66 and 67 show horizontal split heads, field welds, shell, tire 22 not centered on rail and wear on one side of rail 2. Information from these may be used for automatic tracking.

Beams 68 and 69 are, also, produced by the transducer assembly 24. They examine the rail head 4. Such beams 68 and 69 are directed downward at approximately 70 degrees to the vertical, and viewed from above, are inclined at about 10 degrees to the transverse axis of the rail 2.

FIG. 2 is a schematic top view of transducer assembly 14. Transducer assembly 14 is attached to a positioning means 16 at flange 13. Transducer 31 generates the beam 51 and transducer 32 generates the beam 52. Transducers 33 and 34 generate beams 53 and 54, respectively. Transducer 35 generates the beam 55 and transducer 36 generates the beam 56. Transducer 37 generates the beam 57. Transducer 38 generates beam 58 and transducer 39 generates beam 59.

Figure 3:
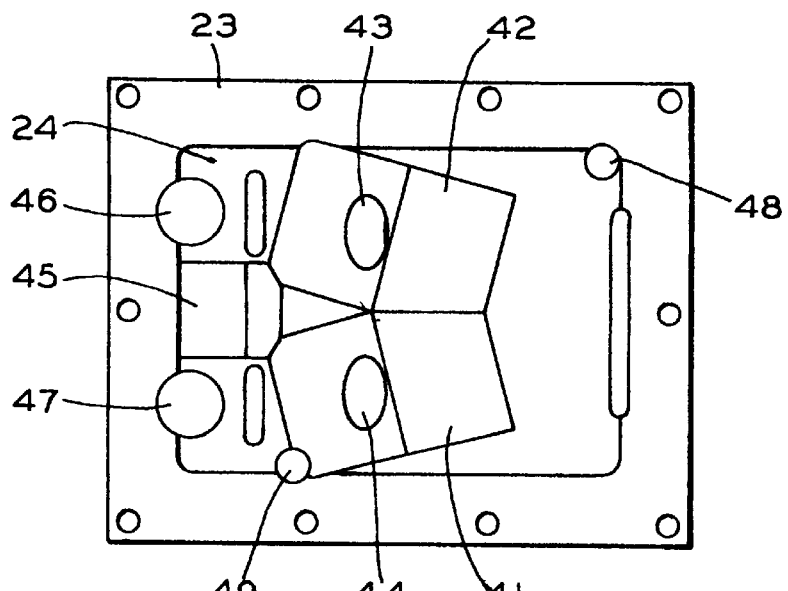
FIG. 3 is a schematic top view illustrating an acoustic transducer assembly module used in a second one of the two tires.

FIG. 3 is a schematic top view of transducer assembly 24. Transducers 41 and 42 generate beams 61 and 62, respectively. Transducers 43 and 44 generate beams 63 and 64, respectively. Transducer 45 generates the beam 65. Transducers 46 and 47 generate the beams 66 and 67. Transducer 48 generates beam 68 and the transducer 49 generates beam 69.

Figure 4:
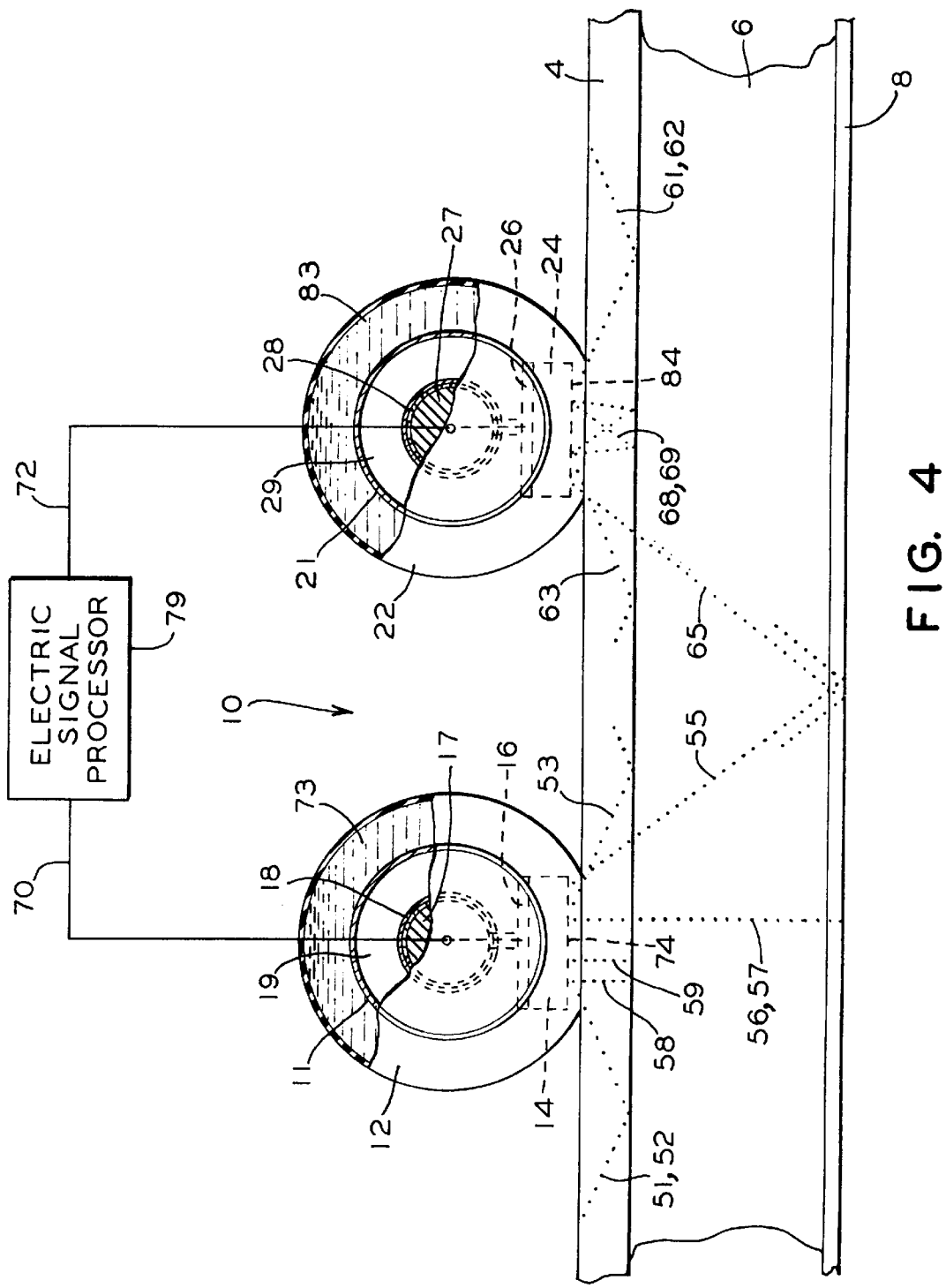
FIG. 4 shows cabling from the transducers to the electric signal processing means.

The transducers are connected to electric signal processing means by cables (shown in FIGS. 4 & 5) which pass through the axles 17 and 27. The transducers in transducer assembly 14 are connected by cable 70 through axle 17 to electric signal processing means 79. Likewise, the transducers in transducer assembly 24 are connected by cable 72 through axle 27 to electric signal processing means 79. Two presently preferred arrangements for connecting the cables are presented in Table 1, which follows. One of these arrangements uses 16 channels and the other arrangement uses 8 channels.

TABLE 1

| 16 CHANNEL | | 8 CHANNEL | | |
|---|---|---|---|---|
| 31 | 41 | 31 | + | 41 |
| 32 | 42 | 32 | + | 42 |
| 33 | 43 | 33 | + | 34 |
| 34 | 44 | 43 | + | 44 |
| 35 | 45 | 35 | | 45 |
| 36 + | 37 | 36 | + | 37 |
| 46 | 47 | | | |
| 38 | 39 | | | |
| 48 + | 49 | 48 | + | 49 |

In the 16 channel arrangement, the transducers 31–35, 38 and 39 are individually connected to one of the sixteen channels. Transducers 36 and 37 are both connected to a single channel. Likewise, in the 16 channel arrangement, transducers 41 to 47 are individually connected to one of the 16 channels. Transducers 48 and 49 are both connected to a single channel.

In the 8 channel arrangement, the transducer 35 and transducer 45 are individually connected to one of the 8 channels. Transducers 31 and 41 are both connected to one channel, transducers 32 and 42 are both connected to one channel, transducers 33 and 34 are both connected to one channel, transducers 43 and 44 are both connected to one channel, transducers 36 and 37 are both connected to one channel, and transducers 48 and 49 are both connected to one channel.

The transducer assemblies 14 and 24 are plastic blocks which have sockets machined therein into which the transducers are mounted. The presently preferred material employed for the blocks will be chosen for its easy machining properties and for its excellent stability in a water-based environment.

The sockets are formed with flat bottom surfaces on which the transducers are cemented, for example, by an epoxy resin. It is necessary to have a good acoustic connection between the transducers and the blocks.

The sockets are machined with a variety of orientations, which depend upon the orientation of the acoustic beams which are required. The acoustic beam in the plastic has the direction of the normal to the flat on which the transducer is mounted.

For the acoustic beams for which precise control of angle is required, notably beams 51, 52, 61, and 62, the beam from the transducer passes first through the plastic to encounter the bottom surface of the plastic of the block, second through a layer of liquid, then through the thickness of the tire material, and then finally into the rail 2. FIG. 1 shows bottom surface 74 of transducer assembly 14, and bottom surface 84 of transducer assembly 24.

For acoustic beams for which precise control of angle is not necessary, the acoustic beam may pass through the plastic, then through a wedge of water under the block, then through the tire material into the rail 2. This arrangement is used when necessary to save space in the block. This does introduce some dependency of beam direction on the speed of sound in the water, but is only used when the beam angle in the steel is not critical.

To define the exact angle at which the sockets are to be machined to obtain beams having a desired orientation in the rail, refraction must be considered between the interface where the beam leaves the plastic into the liquid, and again the interface between the liquid and the tire material.

To calculate the angles of refraction, the relative speeds of sound are required. The velocity of a longitudinal acoustic wave in the plastic is 2.26 millimeters per microsecond. This is to be compared with the velocity of a transverse wave in the steel rail.

Similar considerations apply both to the projection of acoustic beams from a transducer, then through plastic, water, tire material and into the steel, and return signals from the steel through the tire material, water, and plastic to the transducer. If a point in the steel rail is illuminated by a beam from a specific transducer, then an acoustic wave reflected by an imperfection at that point can be detected by the same transducer. One can think of a specific transducer and a specific beam in the steel as converting energy, either from the transducer to the beam, or from the beam to the transducer.

The divergence of the beams, and hence their effective length, depends on the wavelength of the acoustic beam compared to the size of the transducer. Transducers 31, 32, 41 and 42 are made as large as possible, more than 20 millimeters in size to obtain relatively small divergence beams, and hence beams with a long effective length. At a frequency of 2.25 mhz, the beam diverges at approximately 0.1 radians.

The other transducers have smaller sizes than these, and hence have beams with greater divergence. When it is necessary to reduce the divergence of their beams, or improve resolution, a frequency of 5.0 mhz is used. For example, 5.0 mhz may be used for transducers 38, 39, 48 and 49.

All of the transducers are pulsed at the same instant, both the 2.25 mhz, and the 5.0 mhz. This is in order to maximize the quiet times when signals can be received back from the rail, thereby increasing the maximum test speed.

In this embodiment, the transducer assemblies 14 and 24 have widths of approximately 3.25 inches, and lengths of approximately 4.0 inches.

The sockets in which the transducers are placed are sealed to exclude the liquid in the tire because of the high Voltages (eg 650 Volts) which are applied to the electrical leads attached to the transducers.

The tire may have a diameter of approximately 8 inches. It is pressed against the rail 2 so as to have a flattened portion where the tire contacts the rail 2 of approximately four inches. The tire is preferably made of polyurethane, the wall thickness being approximately 1/16". For mounting on the vehicle, the axles 17 and 27 of the tires are made so they can be raised so the tires do not contact the terrain on which the vehicle travels after it leaves the rails 2.

The electric signal processing means is responsible for generating the high frequency pulses of electric energy which energize the transducers. The electric signal processing means are also responsible for interpreting the electric signals returned from the transducers, which contain information regarding defects in the rail 2. Such electric signal processing means may provide indications of defects such as directing a paint spraying means to mark defective area of the rail 2. The electric signal processing means may also provide a display to an operator of the vehicle, or store the information in a memory storage device. In the latter case, navigational information, such as data from a global positioning system or milepost data may be recorded along with information regarding defects.

Figure 5:
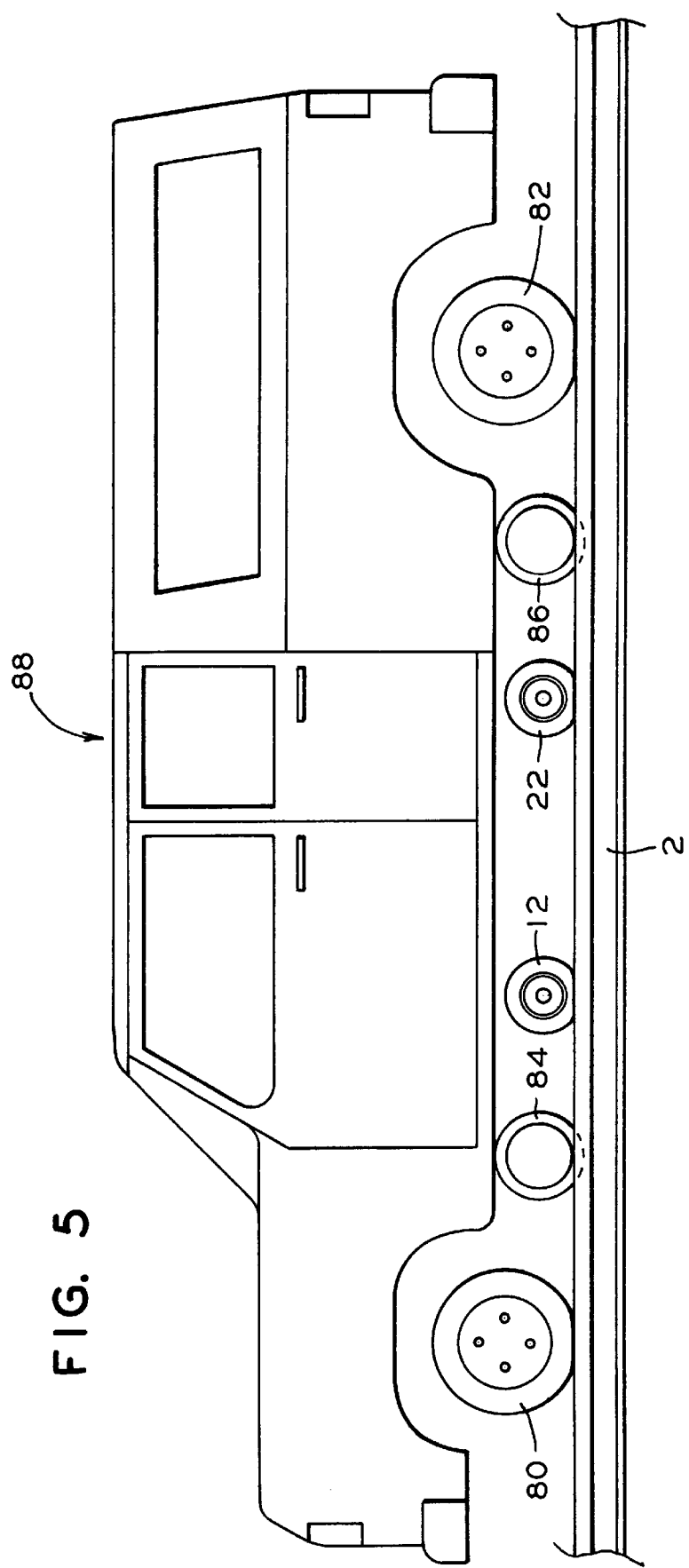
FIG. 5 shows the test vehicle.

FIG. 5 shows vehicle 88 with tires 12 and 22 containing sensors. The vehicle has rubber tires 80 and 82 and flanged wheels 84 and 86 which serve as guide means for keeping the vehicle on the rails. Tires 12 and 22 and guide means 84 and 86 are lifted when the vehicle is driven off the rails.

Now discussing the invention more broadly, there is disclosed an apparatus for detecting, providing indications and recording the location of certain types of defects detected in an object. Such apparatus includes an engagement means consisting of a tire for rolling contact with the object, the tire containing a liquid. Means are connected to the tire for supporting it and for rolling it along the object. An acoustic transducer assembly is located inside the tire. Means are connected to the transducer assembly to position it in the tire adjacent a part of the tire in contact with the object. The liquid acts as an acoustic bridge between the acoustic transducer assembly and the tire. An electric signal processing means is connected to the transducer assembly. The transducer assembly provides conversion of energy between electric signals in the electric signal processing means and acoustic signals in the object. The electric signals are for placing acoustic signals in the object and/or for interpretation of acoustic signals returned from the object.

The object observed for defects by this apparatus may be elongated, in which case acoustic beams may be defined in relation to a major axis of the object. Beams may, for example be applied to the object, the beams directed at a predetermined angle relative to the major dimension of the object. They may, for example, be approximately parallel to the object. The beam may also have a direction at a predetermined angle relative to a minor dimension of the object.

The electric signal processing means may generate pulses of high frequency electric energy followed by quiet times. The transducers converting the pulses of high frequency electric energy into pulses of ultrasonic acoustic energy. The pulses of ultrasonic energy coupled into the object return acoustic signals from the object containing information regarding imperfections in the object. The transducers convert the returned acoustic energy into return electric signals which provide information regarding imperfections in the object. The apparatus may also include means for displaying signals indicating such imperfections in the object.

The acoustic transducer assembly may be formed from a block of plastic having a pocket formed in it and a planar surface in the pocket and a transducer cemented against the planar surface to provide good acoustic contact between the transducer and the block. The planar surface of the pocket may be machined at a predetermined angle relative to the surface which contacts the inside surface of the tire to provide a predetermined direction for the acoustic beam in the plastic block and hence a predetermined direction for the beam refracted into the object.

In another aspect, the invention provides for ultrasonic inspection of one or more rails of a pair of railroad rails. The apparatus includes a vehicle which can travel along the pair of rails. It has an engagement means consisting of a tire attached to the vehicle for rolling contact with one of the rails. The tire contains a liquid and a transducer assembly. Means is attached to the vehicle for positioning the transducer assembly inside the tire. The liquid and the portion of the tire in contact with the rail acting as an acoustic bridge between the transducer assembly and the rail. An electric signal processing means is located on the vehicle and connected to the transducer assembly. The transducers serve to convert energy between electric signals in the electric signal processing means and acoustic signals in the rail, the electric signals for placing acoustic signals in the rail and/or for interpreting acoustic signals returned from the rail.

The apparatus may include at least one transducer oriented at a predetermined angle relative to the lengthwise dimension of the rail. The transducer interchanges electric energy between the electric signal processing means and acoustic signals in the rail. The acoustic signals having a predetermined orientation relative to the lengthwise dimension of the rail. The predetermined orientation of the transducer would be determined considering refraction between the block and the rail. The beam direction may be approximately parallel to the lengthwise dimension of the rail.

The beam may be angled downward and be reflected from the lower surface of the rail head (above the web of the rail). It would be reflected upward to illuminate deep imperfections which would otherwise be obscured by surface imperfections in the rail. The surface imperfections, for example, may be shelling, which is laminar cracks just under the wear surface of the rail, which are caused by fatigue cycling due to passage of load bearing wheels.

Two transducers may be used and these may create beams in the rail which cross the centerline of the rail at a small angle, while descending to bounce off the lower surface of the rail head to illuminate deep imperfections which would otherwise be obscured by surface imperfections.

The apparatus may further include a transducer mounted at a predetermined angle relative to the widthwise dimension of the rail. This transducer interchanges energy between electric signals in the electric signal processing means and an acoustic beam in the rail, which has a predetermined direction relative to the widthwise dimension of the rail.

The electric signal processing means produces pulses of high frequency electric energy followed by quiet times. The transducer assembly converts the pulses of high frequency electric energy into pulses of ultrasonic energy, which are coupled into the rail. The transducer assembly also receives acoustic energy back from the rail. The acoustic energy indicating imperfections in the rail, the transducer assembly converting the acoustic energy into electrical signals which the electric signal processing means uses to generate signals indicative of imperfections. Means may be provided for these to be displayed.

The transducer assembly may be formed from a block of plastic with a pocket formed in it, the pocket having a planar surface onto which a transducer is cemented for good acoustic contact between the transducer and the block. The planar surface in the pocket is inclined at a predetermined angle relative to the bottom surface, so that the transducer cemented into the pocket projects an acoustic beam oriented at a predetermined angle for refraction into the rail at a predetermined angle.

The apparatus may also include a transducer which projects a beam downward for reflection of the lower surface of the rail head on one side of the rail, and is bounced approximately horizontally to bounce off the lower surface of the rail head on the other side of the rail and then upward to another transducer. This arrangement provides for detecting flaws at the elevation of the bottom of the rail head. Such a flaw, for example, could be a vertically split head.

The apparatus may further include a transducer which sends an acoustic beam downward through the web to be reflected off the bottom surface of the rail. Such a beam may detect such flaws as bolt hole cracks.

The apparatus may include a pair of tires mounted in tandem on the same rail. A transducer disposed in one of the tires would project a beam downward and toward the other tire, the beam penetrating the web, bouncing off the lower surface of the rail, and being detected by a transducer disposed in the other tire. This would provide observation of flaws in the web such as bolt hole cracks.

The vehicle on which this system is preferably mounted on rubber tires so that it can drive onto or off of the rails which the system is to examine. The vehicle includes guide means disposed thereon which can contact the gauge surface of the rails to guide the tires and keep the vehicle on the rails. These guide means would be elevated when the vehicle operates off the rails. The tire or tires containing the transducers would also be elevated for travel off the rails, to prevent contact between these tires and the terrain.

In an additional aspect, this invention provides a method for ultrasonic inspection of an object. The method includes rolling an engagement means such as a tire along the surface of the object. The tire contains both a liquid and a transducer assembly. The transducer assembly is placed adjacent a portion of the tire in contact with the surface of the object. The liquid provides an acoustic bridge between the transducer assembly and the tire. The transducer assembly has at least one transducer which is firmly attached to it.

The method includes applying high frequency electrical pulses to the transducer to induce it to generate ultrasonic pulses which create ultrasonic beams which pass through the transducer assembly, the liquid and the tire into the object. The beam encounters imperfections in the object and generates back reflected acoustic signals which indicates the imperfections. The back reflected acoustic signals returning to the transducer to generate electric signals which indicate the imperfections. The method includes transmitting the electric signals which indicate imperfections to an electric signal processing means which then defines and provides indication of the imperfections.

The object being examined may be an elongate object and it may be a rail of a railroad. In this case, the ultrasonic beam is projected into the rail at a direction which is approximately parallel to the centerline of the rail. The ultrasonic beam may be projected at an angle sloping downward to be reflected off the lower surface of the rail head to produce an upward reflected beam which illuminates deep defects otherwise hidden underneath surface imperfections. These deep defects providing a back reflected acoustic signal. The method may also include projecting such a beam across the width of the rail head to bounce off the lower surface of the rail head on opposite sides of the rail to illuminate deep defects on the opposite sides of the rail. The method may further include projecting two such beams, projected from opposite sides of the rail to the opposing sides of the rail at the lower surfaces of the rail head, thereby illuminating deep defects on both sides of the rail.

The method may also include projecting a beam steeply downward on the centerline of the rail to illuminate the web and bottom flange of the rail, and the method may include receiving a reflected acoustic signal which shows imperfections in the web and bottom flange of the rail.

While both a presently preferred and various alternative embodiments of the invention have been described in considerable detail above it should be recognized that various other adaptations and modifications of the invention may be made by those persons skilled in the rail testing art without departing from either the spirit of the invention or the scope of the appended claims.

In the following claims, the adjective "such" has been used to refer back to previously cited things which are not part of the invention itself, but rather are part of the environment for which the invention is intended. The adjective "said" is used to refer back to parts of the invention itself.

I claim:

1. An ultrasonic testing device for detecting flaws present in a predetermined object, said testing device comprising:
   (a) an engagement means for rolling contact with such predetermined object;
   (b) a predetermined liquid disposed within said engagement means for providing a coupling medium;
   (c) a support means connected to said engagement means for supporting said engagement means in an operating position with respect to such predetermined object;
   (d) a rotary bearing means connected to said support means for enabling said engagement means to be in rolling contact with such predetermined object;
   (e) at least one acoustic transducer assembly positioned within said engagement means, said at least one acoustic transducer assembly consisting of a block having acoustic transducers affixed to said block, said acoustic transducers in acoustic contact with said block, said block having a surface portion substantially parallel to and adjacent to a portion of said engagement means in contact with such predetermined object, a layer of said predetermined liquid and said portion of said engagement means in contact with such predetermined object providing an acoustic bridge between said block and such predetermined object; and
   (f) at least one electrical signal processing means connected to said at least one acoustic transducer assembly for generating and communicating a plurality of first electrical signals to said at least one acoustic transducer assembly and receiving a plurality of second electrical signals for analysis from said at least one acoustic transducer assembly, said at least one acoustic transducer assembly converting said plurality of first electrical signals received from said at least one electrical signal processing means into a plurality of first acoustic signals and communicating said plurality of first acoustic signals to such predetermined object and converting a plurality of second acoustic signals received from such predetermined object into said plurality of second electrical signals and communicating said plurality of second electrical signals to said at least one electrical signal processing means for analysis.

2. An ultrasonic testing device, according to claim 1, wherein such predetermined object is an elongated object.

3. An ultrasonic testing device, according to claim 2, wherein said at least one acoustic transducer assembly includes at least one transducer mounted at a predetermined angle relative to a major dimension of such elongated object, said at least one transducer for interchanging electric energy between said electrical signal processing means and said plurality of first acoustic signals in such elongated object, each of said plurality of first acoustic signals having a particular beam direction defined by said predetermined angle relative to said major dimension of such elongated object, and by refraction of said plurality of first acoustic signals between said at least one acoustic transducer assembly and such elongated object.

4. An ultrasonic testing device, according to claim 3, wherein said beam direction of said plurality of first acoustic signals is approximately parallel to such elongated object.

5. An ultrasonic testing device, according to claim 2, wherein said acoustic transducer assembly includes at least one transducer mounted at a predetermined angle relative to a minor dimension of such elongated object, said at least one transducer for interchanging electric energy between said electric signal processing means and acoustic signals in such elongated object, said acoustic signals having a particular beam direction defined by said predetermined angle relative to said minor dimension of such elongated object and by refraction of acoustic signals between said acoustic transducer assembly and such elongated object.

6. An ultrasonic testing device, according to claim 2, wherein said electric signal processing means generates pulses of high frequency electric energy followed by quiet times, said transducer assembly converting said pulses of said high frequency electric energy into pulses of ultrasonic acoustic energy, said pulses of said ultrasonic acoustic energy coupled into such elongated object, said transducer assembly receiving acoustic energy returned from such elongated object, said acoustic energy returned from such elongated object indicative of imperfections in such elongated object, said transducer assembly converting said acoustic energy returned from such elongated object into return electrical signals, said electric signal processing means generating signals indicative of imperfections in such elongated object.

7. An ultrasonic testing device, according to claim 6, wherein said ultrasonic testing device further includes a means for displaying signals indicative of such imperfections in such elongated object.

8. An ultrasonic testing device, according to claim 2, wherein said at least one acoustic transducer assembly is formed from a block of plastic having at least one pocket formed therein for retaining at least one transducer, said at least one pocket having at least one planar surface, said at least one transducer being cemented onto said planar surface in said at least one pocket to enhance acoustic contact with said block.

9. An ultrasonic testing device, according to claim 8, wherein at least one of said planar surface in said at least one pocket is inclined at a predetermined angle relative to said block, whereby said at least one transducer cemented onto said planar surface projects an acoustic beam at a predetermined angle into said block for refraction into said elongated object at a predetermined angle.

10. An apparatus for ultrasonic inspection of at least one rail disposed in a railroad track structure, said apparatus comprising:
   (a) a vehicle for travelling along such railroad track structure;
   (b) an engagement means for rolling contact with such at least one rail;
   (c) a predetermined liquid disposed within said engagement means for providing a coupling medium;
   (d) a support means connected to said engagement means for supporting said engagement means in an operating position with respect to such at least one rail;
   (e) a rotary bearing means connected to said support means for enabling said engagement means to be in rolling contact with such at least one rail;
   (f) at least one acoustic transducer assembly positioned within said engagement means, said at least one acoustic transducer assembly consisting of a block having acoustic transducers affixed thereto, said acoustic transducers in acoustic contact with said block, said block having a bottom surface portion substantially parallel to and adjacent to a portion of said engagement means in contact with such at least one rail, a layer of said predetermined liquid and said portion of said engagement means in contact with such at least one rail providing an acoustic bridge between said block and such at least one rail; and (g) at least one electrical signal processing means disposed on such vehicle, said at least one electrical signal processing means connected to said at least one transducer assembly for generating and communicating a plurality of first electrical signals to said at least one transducer assembly and receiving a plurality of second electrical signals for analysis from said at least one transducer assembly, said at least one acoustic transducer assembly converting said plurality of first electrical signals received from said at least one electrical signal processing means into a plurality of first acoustic signals and communicating said plurality of first acoustic signals to such at least one rail and converting a plurality of second acoustic signals received from such at least one rail into said plurality of second electrical signals and communicating said plurality of second electrical signals to said at least one electrical signal processing means for said analysis.

11. An apparatus for ultrasonic inspection of rail disposed in a railroad track structure, according to claim 10, wherein said acoustic transducer assembly includes at least one transducer mounted at a predetermined angle relative to a major dimension of such railroad rail for interchanging electric energy between said electric signal processing means and said plurality of first acoustic signals in such railroad rail, said plurality of first acoustic signals having a particular beam direction defined by said predetermined angle relative to said major dimension of such railroad rail, and by refraction of acoustic signals crossing said acoustic bridge between said acoustic transducer assembly and such railroad rail.

12. An apparatus for ultrasonic inspection of rail disposed in a railroad track structure, according to claim 11, wherein said beam direction of said plurality of first acoustic signals is approximately parallel to such railroad rail.

13. An apparatus for ultrasonic inspection of rail disposed in a railroad track structure, according to claim 12, wherein said beam descends into such rail and is reflected from a lower surface of such rail head, thereby being reflected upward to encounter deep imperfections lying underneath surface imperfections which would otherwise prevent observation of such deep imperfections.

14. An apparatus for ultrasonic inspection of rail disposed in a railroad track structure, according to claim 13, wherein said apparatus includes a pair of transducers oriented at a predetermined transducer angle relative to such rail to exchange electric energy with acoustic energy in a pair of beams each crossing a centerline of such rail to observe deep imperfections lying underneath surface imperfections which would otherwise prevent observation of such deep imperfections.

15. An apparatus for ultrasonic inspection of rail disposed in a railroad track structure, according to claim 10, wherein said acoustic transducer assembly includes at least one transducer mounted at a predetermined angle relative to a width dimension of such railroad rail for interchanging electric energy between said electric signal processing means and acoustic signals in such railroad rail, said acoustic signals having a particular beam direction defined by said predetermined angle relative to said width dimension of such railroad rail and by refraction of acoustic signals between said acoustic transducer assembly and such railroad rail.

16. An apparatus for ultrasonic inspection of rail disposed in a railroad track structure, according to claim 10, wherein said electric signal processing means generates pulses of high frequency electric energy followed by quiet times, said transducer assembly converting said pulses of said high frequency electric energy into pulses of ultrasonic acoustic energy, said pulses of said ultrasonic acoustic energy coupled into such railroad rail, said transducer assembly receiving acoustic energy returned from such railroad rail indicative of imperfections in such railroad rail, said transducer assembly converting said acoustic energy returned from such railroad rail into return electrical signals, said electric signal processing means generating signals indicative of imperfections in such railroad rail.

17. An apparatus for ultrasonic inspection of rail disposed in a railroad track structure, according to claim 16, wherein said apparatus further includes a means for displaying signals indicative of such imperfections in such railroad rail.

18. An apparatus for ultrasonic inspection of rail disposed in a railroad track structure, according to claim 10, wherein said transducer assembly is formed from a block of plastic having at least one pocket formed therein for retaining at least one transducer, said at least one pocket having at least one planar surface, said at least one transducer cemented onto said at least one planar surface in said at least one pocket to enhance acoustic contact with said block.

19. An apparatus for ultrasonic inspection of rail disposed in a railroad track structure, according to claim 18, wherein said at least one planar surface in said at least one pocket has a surface inclined at a predetermined angle relative to said block, whereby said at least one transducer cemented onto said at least one planar surface projects an acoustic beam at a predetermined angle into said block, said acoustic beam for refraction into such railroad rail at a predetermined angle.

20. An apparatus for ultrasonic inspection of rail disposed in a railroad track structure, according to claim 15, wherein said at least one transducer is oriented such that it exchanges energy with an acoustic beam which is reflected off a lower surface of a head of such railroad rail, crosses such rail approximately horizontally, and is then reflected upward from a second lower surface of such head of such railroad rail, thereby detecting flaws at an elevation of a bottom of such head of such railroad rail.

21. An apparatus for ultrasonic inspection of rail disposed in a railroad track structure, according to claim 19, wherein said acoustic beam is directed steeply downward to penetrate a web of such railroad rail thereby detecting at least one of bolt hole flaws and other web imperfections.

22. An apparatus for ultrasonic inspection of rail disposed in a railroad track structure, according to claim 21, wherein said apparatus includes a pair of tires mounted in tandem on such rail, said beam originating in a first transducer disposed in a first one of said pair of tires, passing downward into such web, being reflected off a bottom surface of such rail, and being detected by a second transducer disposed in a second one of said pair of tires.

23. An apparatus for ultrasonic inspection of rail disposed in a railroad track structure, according to claim 10, wherein said vehicle travels on such pair of railroad rails on a set of second tires, said vehicle including means in contact with a pair of gauge surfaces of such rails to guide said set of second tires to follow such rails, said vehicle capable of driving off of such rails and climbing back onto such rails.

24. A method for ultrasonic inspection of an object, said method comprising the steps of:

(a) contacting a first surface of said object to be tested with an engagement means containing a predetermined coupling medium and at least one acoustic transducer assembly therein said at least one transducer assembly consisting of a block having acoustic transducers affixed thereto, said acoustic transducers in acoustic contact with said block, said block having a surface portion substantially parallel to and positioned adjacent at least a portion of said engagement means in contact with said object, a layer of said predetermined liquid and said portion of said engagement means in contact with said object providing an acoustic bridge between said block and said object;

(b) supporting said engagement means in rolling contact with said first surface of said object;

(c) moving said engagement means containing said coupling medium and said at least one acoustic transducer assembly over a predetermined path on said object;

(d) generating a plurality of first electrical signals in at least one electrical signal processing means;

(e) communicating said plurality of said first electrical signals generated in step (d) to said at least one acoustic transducer assembly;

(f) converting said plurality of first electrical signals communicated to said at least one acoustic transducer assembly in step (e) into a plurality of first acoustic signals;

(g) communicating said plurality of first acoustic signals generated in step (f) to said object;

(h) receiving a plurality of second acoustic signals from said object in at least one acoustic transducer;

(i) converting said plurality of second acoustic signals received by said at least one transducer in step (h) into a plurality of second electrical signals;

(j) communicating said plurality of second electrical signals generated in step (i) to said electrical signal processing means; and (k) analyzing said plurality of second electrical signals in said electrical signal processing means for detecting flaws present in said object.

25. A method for ultrasonic inspection of an object, according to claim 24, wherein said object is an elongated object.

26. A method for ultrasonic inspection of an object, according to claim 25, wherein said elongated object is at least one rail of a railroad track structure.

27. A method for ultrasonic inspection of an object, according to claim 26, wherein said plurality of first acoustic signals is an ultrasonic beam which is approximately parallel to a centerline of such rail.

28. A method for ultrasonic inspection of an object, according to claim 27, wherein said ultrasonic beam slopes downward and is reflected off a lower surface of a railhead of such rail to produce an upward reflected beam, said upward reflected beam illuminating deep defects otherwise hidden underneath surface imperfections, said deep defects causing said back reflected acoustic signal.

29. A method for ultrasonic inspection of an object, according to claim 28, wherein said ultrasonic beam is generated by a transducer on a first side of a centerline of such rail and is directed across such centerline of such rail to illuminate deep defects in a second opposite side of such centerline of such rail.

30. A method for ultrasonic inspection of an object, according to claim 29, wherein said method includes the additional step of generating a second ultrasonic beam by a second transducer on a second side of such centerline of such rail, said second ultrasonic beam being directed across such centerline to such first side of such centerline.

31. A method for ultrasonic inspection of an object, according to claim 26, wherein said ultrasonic beam is directed steeply downward, thereby illuminating a web and a bottom flange of such railroad rail, whereby said back reflected acoustic signal is indicative of imperfections in such web and such bottom flange of such railroad rail.

32. An ultrasonic testing device for detecting flaws in a railroad rail, said device comprising:

(a) an engagement means mounted to be rolled along such railroad rail;

(b) a transducer assembly disposed within said engagement means, said transducer assembly consisting of a block of material having at least one acoustic transducer attached to said transducer assembly, said at least one acoustic transducer mounted in acoustic contact with said block at a predetermined orientation in relation to said block to generate an acoustic beam having a predetermined direction in said block, said block having a bottom surface portion, said block positioned within said engagement means so that said bottom surface portion of said block is adjacent a portion of said engagement means in contact with such rail;

(c) a liquid disposed in said engagement means so that a liquid layer is provided between said bottom surface portion of said block and said portion of said engagement means in contact with such rail, so that said liquid layer and said portion of said engagement means in contact with such rail act as an acoustic bridge between said block and such rail to communicate said at least one acoustic beam from said block into such rail and to communicate reflected acoustic signals from such rail back to said block and thence to said at least one transducer, so that said at least one acoustic beam in such rail is oriented at a predetermined angle, which is substantially independent of a speed of sound in said liquid;

(d) means connected to said at least one transducer for providing electrical signals for generation of said acoustic beams; and (e) means connected to said at least one transducer for receiving electrical signals indicative of said reflected acoustic signals, and for processing said electrical signals to provide signals indicative of such flaws in such rail.

* * * * *